(12) United States Patent
Baumgart et al.

(10) Patent No.: US 8,404,273 B2
(45) Date of Patent: Mar. 26, 2013

(54) WOUND CARE SYSTEM AND BACTERICIDAL METHODS AND DEVICES

(75) Inventors: Helmut Baumgart, Yorktown, VA (US); Diefeng Gu, Yorktown, VA (US)

(73) Assignee: Old Dominion University Research Foundation, Norfolk, VA (US)

( * ) Notice: Subject to any disclaimer, the term of this patent is extended or adjusted under 35 U.S.C. 154(b) by 288 days.

(21) Appl. No.: 12/766,706

(22) Filed: Apr. 23, 2010

(65) Prior Publication Data
US 2010/0274176 A1  Oct. 28, 2010

Related U.S. Application Data

(60) Provisional application No. 61/172,636, filed on Apr. 24, 2009.

(51) Int. Cl.
*A61F 13/00* (2006.01)
*A61K 9/70* (2006.01)
*A61L 15/16* (2006.01)
*A61L 15/00* (2006.01)

(52) U.S. Cl. ........ 424/443; 424/444; 424/445; 424/446; 424/447; 424/449

(58) Field of Classification Search .................. 424/443, 424/444, 445, 446, 447, 449
See application file for complete search history.

(56) References Cited

U.S. PATENT DOCUMENTS

| | | | | |
|---|---|---|---|---|
| 4,571,241 A | * | 2/1986 | Christopher | 604/104 |
| 5,681,575 A | * | 10/1997 | Burrell et al. | 424/423 |
| 2007/0009586 A1 | * | 1/2007 | Cohen et al. | 424/445 |
| 2008/0039768 A1 | * | 2/2008 | Francis | 604/8 |

OTHER PUBLICATIONS

Ohko et al. "Self-Sterilizing and Self-Cleaning of silicone Catheters Coated with TiO2 Photocatalysts Thin Films: A Preclinical Work", J. Biomed Mater Res (Appl Biomater) 58: 97-101, 2001.*

* cited by examiner

*Primary Examiner* — Isis Ghali
(74) *Attorney, Agent, or Firm* — Novak Druce Connolly Bove + Quigg LLP

(57) ABSTRACT

A variety of article and systems including wound care systems, methods for making the wound care systems, bactericidal, and methods for treating wounds using these systems are disclosed. The wound care systems may include a first material comprising one or more fibers or porous media. The one or more fibers or porous media may be coated with a second material that is capable of inhibiting the growth of bacteria and killing the bacteria to render the wound care system sterile, increasing the absorbency of the first material, or both upon exposure to light. The first material may be cotton, or any suitable fibrous material, the second material may be $TiO_2$, and the light may be UV or visible light. A variety of methods including ALD may be used to coat the first material.

15 Claims, 1 Drawing Sheet

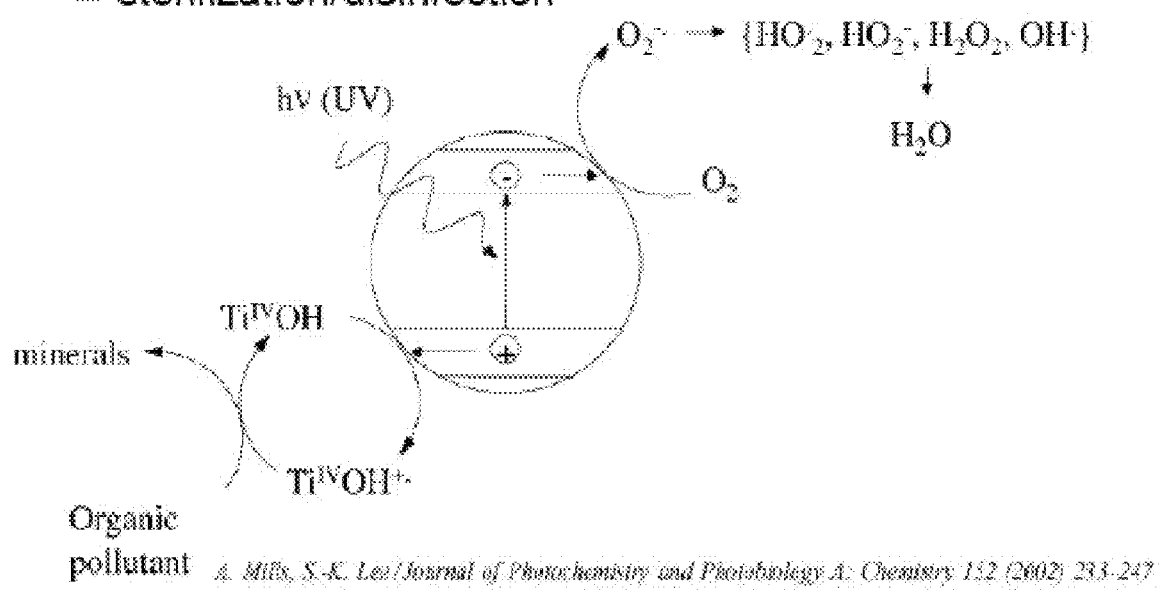

WOUND CARE SYSTEM AND BACTERICIDAL METHODS AND DEVICES

RELATED APPLICATIONS

This application claims priority to U.S. provisional application Ser. No. 61/172,636, filed Apr. 24, 2009, which is hereby incorporated by reference in its entirety.

BACKGROUND

A need exists for better methods and articles for inhibiting the growth of and killing bacteria including bactericidal methods and devices. For example, a basic method of wound treatment involves covering a wound with a wound dressing. The wound dressing may be a precut sheet of a single or multi-layer material having a variety of shapes and sizes. The wound dressing is applied to cover the wound and, sometimes, a portion of the surrounding healthy skin. Some of the principles of wound treatment include absorbing blood and other bodily fluids, keeping the wound and/or the surrounding healthy skin dry, and/or controlling or eliminating bacterial growth. However, many conventional wound dressings are limited in their ability to absorb fluids, maintain dryness, and control bacterial growth.

SUMMARY

Provided herein are, among other embodiments, wound care systems, methods for making the wound care systems, and methods for treating wounds using the wound care systems. Other bactericidal embodiments described hereinafter are for other applications besides wound care.

The disclosed wound care systems are capable of, for example, inhibiting the growth of bacteria (including killing the bacteria) or increasing the absorbency of certain materials of the wound care system, or both, upon exposure to light. Thus, the wound care systems are capable of keeping wounds treated with such systems more dry and more sterile than conventional wound dressings. The electromagnetic radiation exposure time can be varied to achieve a desired degree of inhibiting growth of or killing bacteria.

In one aspect, wound care systems are provided. The wound care system may include a first material comprising one or more fibers, wherein the one or more fibers are coated with a second material. The second material may be capable of inhibiting the growth of bacteria, including killing bacteria, increasing the absorbency of the first material, or both, upon exposure to light. The electromagnetic radiation exposure time can be varied to achieve a desired degree of inhibiting growth of or killing bacteria. The composition of the first material and the second material may vary. Non-limiting examples of such materials are provided herein. In some embodiments, the first material may comprise cotton, silk, or a polymer. However, cotton, silk, or polymer are only representative embodiments. Any fibrous or nanoporous material can be used, including materials comprising nanofibers and/or nanopores. In some embodiments, the second material may comprise a metal oxide, including, but not limited to $TiO_2$. The thickness of the coating of the second material on the one or more fibers of the first material may vary. The wound care systems may be exposed to varying wavelengths of light, including, but not limited to UV light. The wound care systems may include other components, including, but not limited to a light source and, possibly, a programmable switching circuit. Non-limiting examples of light sources are provided herein.

In another aspect, methods for making the wound care systems are provided. The method may include coating one or more fibers of a first material comprising the one or more fibers with a second material, wherein the second material is capable of inhibiting the growth of bacteria, increasing the absorbency of the first material, or both, upon exposure to light. A variety of techniques for coating the one or more fibers may be used. In some embodiments, the one or more fibers are coated using atomic layer deposition (ALD). The methods may include other steps, including, but not limited to coupling a light source to the first material, and possibly, coupling a programmable switching circuit to the light source. Any fibrous or nanoporous material can be used.

In another aspect, methods for treating a wound are provided. The method may include contacting any of the wound care systems disclosed herein to a wound on a subject. In another embodiment, in which the wound care system comprises a light source coupled to the first material and a programmable switching circuit coupled to the light source, the method further comprises turning the light source on and off. The light source may be turned on whenever needed or may be turned on and off at predetermined intervals. The methods may be used to treat the wounds of a variety of mammalian subjects, including, but not limited to humans.

Also provided herein are articles, including bactericidal articles, that include a first material coated with a second material, wherein the second material is capable of inhibiting the growth of bacteria (including killing bacteria), increasing the absorbency of the first material, or both, upon exposure to light, as well as methods of making articles, and methods of sterilizing articles.

In one aspect, articles are provided. The articles may include a first material coated with a second material, wherein the second material capable of inhibiting the growth of bacteria (including killing bacteria), increasing the absorbency of the first material, or both, upon exposure to light. The composition of the first material and the second material may vary. The first material may comprise fibers. The first material can be, for example, any fibrous or nanoporous material including synthetic polymers, natural polymers, or other materials like carbon fibers. Non-limiting examples of such materials are provided herein. In some embodiments, the second material may comprise a metal oxide, including, but not limited to doped or undoped $TiO_2$. Dopants can include at least one of nitrogen, sulfur, and transition metals such as iron and cobalt. The thickness of the coating of the second material on the one or more fibers of the first material may vary. The articles may be exposed to varying wavelengths of light, including, but not limited to UV light and visible light. The articles may comprise fabric, paper, filters, porous glass filters, wound care dressings made from cotton fibers or other fibers, for example polymer fibers. The articles may also comprise lab coats or surgical equipment such as catheters, or water filters.

In another aspect, methods for making the articles are provided. The method may include coating a first material with a second material, wherein the second material is capable of inhibiting the growth of bacteria, increasing the absorbency of the first material, or both, upon exposure to light. A variety of techniques for coating the first material may be used. In some embodiments, the first material is coated using atomic layer deposition (ALD).

In another aspect, methods of sterilizing are provided. The method may include providing an article comprising a first material coated with a second material, wherein the second material is capable of inhibiting the growth of bacteria, increasing the absorbance of the first material, or both, upon exposure to light, and then exposing the second material to light.

The photocatalytic processes described herein can be activated in air or under water. Hence, water supplies can be treated. Filtration media and filters, including those adapted for use with filtering water, can be coated. The media can be microporous or nanoporous.

BRIEF DESCRIPTION OF THE DRAWINGS

FIG. 1 illustrates the photocatalytic oxidation of organic matter upon exposure of $TiO_2$ to UV (ultraviolet) light.

DETAILED DESCRIPTION

Wound Care Systems

A wound care system may include a first material comprising one or more fibers. The one or more fibers may be coated with a second material which is capable of inhibiting the growth of bacteria, increasing the absorbency of the first material, or both, upon exposure to light. By inhibiting the growth of bacteria it is meant that the rate of growth of bacteria associated with the wound is reduced after the second material is exposed to light relative to the rate of growth of bacteria before the second material is exposed to light. In some embodiments, the growth of bacteria may be reduced to the point that substantially no further growth of bacteria occurs after the second material is exposed to light Inhibiting the growth of bacteria also includes reducing the amount of bacteria that may be associated with the wound after the second material is exposed to light relative to the amount of bacteria before the second material is exposed to light. In some embodiments, the amount of bacteria may be reduced to the point that substantially no bacteria is present after the second material is exposed to light. In some embodiments, the second material is capable of killing or eliminating substantially all, or all, bacteria associated with the wound. In such embodiments, the wound care system provides a bactericidal wound care system. The second material may be capable of inhibiting the growth of (and killing) a variety of types of bacteria, including any type of bacteria associated with the wound. As a non-limiting example, one class of bacteria are those that inhabit hospitals and nursing homes and are resistant to conventional antibiotics. Such bacteria are known collectively as Methillicin Resistant Staphylococcus Aureus (MRSA). A non-limiting specific example of such bacteria is staphylococcus aureus, which causes staph infections. Methods for testing and/or monitoring the growth of these and other bacteria are known. See for example, the descriptions provided in published article to Koseki et al., "Photocatalytic bactericidal action of fluorescent light in a titanium dioxide particle mixture: an in vitro study", *Biomedical Research*, 30 (3) 189-192, 2009, which is hereby incorporated by reference in its entirety herein.

The electromagnetic radiation conditions (e.g., exposure time, wavelength, and the like) for best performance in inhibiting growth of or killing bacteria can be determined by methods known in the art.

By increasing the absorbency of the first material, it is meant that the first material is able to absorb more liquid after the second material is exposed to light relative to the amount of liquid that could be absorbed before the second material is exposed to light. A variety of liquids may be absorbed by the first material, including, but not limited to, water, blood, sweat, and other liquids excreted from a wound. Methods for testing and/or monitoring the absorbency of the first material are known.

The composition of the first material and the second material may vary. The composition of the first material is not particularly limited provided the material comprises one or more fibers. Non-limiting examples of suitable first materials include cotton, cotton gauze, silk, polymer, or a polymer gauze. The first material may be provided in various shapes and sizes. The shape and size may be that which is sufficient to cover a wound. The wound care system may comprise one or more layers of the first material.

Similarly, the composition of the second material is not particularly limited provided the material is capable of inhibiting the growth of bacteria, increasing the absorbency of the first material, or both after the second material is exposed to light. In some embodiments, the second material comprises a metal oxide. A non-limiting example of a suitable metal oxide is $TiO_2$. As described above, the one or more fibers of the first material are coated with the second material. These fibers may be coated so that a thin film of the second material is disposed over each fiber. The thickness of the film may vary, depending upon the material of the fibers. In some embodiments, the thickness may range from about 5 nm to about 30 nm. This includes thicknesses of about 10 nm, about 15 nm, about 20 nm, and about 25 nm. The thickness can be also about 5 nm to about 250 nm, or about 5 nm to about 100 nm. One skilled in the art can determine the best thickness to use for a particular commercial application.

As described above, when the second material is exposed to light, the growth of bacteria is inhibited, the absorbency of the first material is increased, or both. A variety of wavelengths of light may achieve these effects, depending upon the type of second material used. In some embodiments, the wavelength of light is in the visible range. In other embodiments, the wavelength of light is in the ultraviolet (UV) range.

In particular, electromagnetic radiation with a wavelength shorter than that of visible light, but longer than x-rays, in the range of about 10 nm to about 400 nm, and/or energies of about 3 eV to about 124 eV can be used.

Examples of UV light include, as known in the art, the following with associated terminology and approximate wavelengths: ultraviolet A (or long wave, or blacklight, UVA, 400 nm-315 nm), near (NUV, 400 nm-300 nm), ultraviolet B (or medium wave, UVB, 315 nm-280 nm), middle (MUV, 300 nm-200 nm), ultraviolet C, short wave, or germicidal, UVC, 280 nm-100 nm), far (FUV, 200-122 nm), vacuum (VUV 200 nm-100 nm), low (LUV, 100 nm-88 nm), super (SUV, 150 nm-10 nm), and extreme (EUV, 121 nm-10 nm). Another example is deep UV (e.g., less than 300 nm wavelengths). See, for example, ISO-DIS-21348.

One particularly useful range of UV light is 200 nm and higher.

The disclosed wound care systems may further include other components. In some embodiments, the wound care systems may include a light source coupled to the first material. A variety of light sources may be used, depending upon the desired wavelength of light. In some embodiments, the light source includes one or more LEDs. The LEDs may be UV-emitting or visible light emitting LEDs. Techniques for coupling the LEDs to the first material are known. Other embodiments for light source include, for example, artificial light sources, fluorescent lamps, including compact fluorescent lamps (CFLs), incandescent light bulbs, OLEDs, PLEDs, high pressure mercury lamps, halogen lamps, other kinds of lamps emitting UV and/or visible light, and even natural light from the sun.

In other embodiments, the wound care systems may include a programmable switching circuit coupled to the light source. The programmable switching circuit may be capable of turning on and off the light source at predetermined intervals. Such circuits are known, as well as techniques for coupling the circuits to the light sources disclosed above. The length of illumination may vary in order to obtain the desired level of bacteria inhibition. Longer illumination times may eliminate or kill substantially all, or all bacteria associated with a wound.

As described above, the second material is capable of inhibiting the growth of bacteria, increasing the absorbency of the first material, or both, upon exposure to light. These effects are further described below with respect to an exemplary second material, $TiO_2$. FIG. 1 illustrates the photocatalytic oxidation of organic matter upon exposure of $TiO_2$ to UV light. As shown in the figure, a number of possible reactions may occur. For example, the following superoxide radical may be created:

$$O_2 + e^- \rightarrow [O_2]^-$$

In addition, hydroxyl radicals and ozone may be generated:

$$[O_2]^- + H_2O \rightarrow HO_2 + OH^-$$

$$HO_2 + e^- \rightarrow [HO_2]^-$$

$$[OH_2]^- + H_2O \rightarrow H_2O_2 + OH^-$$

These radicals are capable of attacking organic material, including bacteria, and destroying the bacteria through the process of photocatalytic oxidation. These reactions also render the first material "superhydrophilic." In other words, the first material is capable of absorbing more liquid after the second material is exposed to light compared to the amount of liquid that could be absorbed before the second material is exposed to light.

Methods for Making Wound Care Systems

Also provided are methods for making the disclosed wound care systems. In one embodiment, the method comprises coating one or more fibers of a first material comprising the one or more fibers with a second material, wherein the second material is capable of inhibiting the growth of bacteria, increasing the absorbance of the first material, or both, upon exposure to light. The composition and characteristics of the first material and the second material have been described above.

A variety of methods may be used to coat the fibers of the first material. In some embodiments, the fibers may be coated using atomic layer deposition (ALD). ALD is a known technique in other contexts.

Other coating methods including vapor deposition methods such as, for example, CVD (chemical vapor deposition), as well as solution coating and sol gel coating.

ALD can provide accurate, Angstrom control of the coatings. Briefly, ALD technology deposits thin films using pulses of chemical precursor gases to adsorb at the target surface one atomic layer at a time. ALD is based on the sequential deposition of individual monolayers or fractions of a monolayer in a controlled fashion. More specifically, in ALD the growth substrate surface is alternately exposed to the vapors of one of two chemical reactants (complementary chemical precursors), which are supplied to the reaction chamber one at a time. The exposure steps are separated by inert gas purge or pump-down steps in order to remove any residual chemical precursor or its by-product before the next chemical precursor can be introduced into the reaction chamber. Thus, ALD involves a repetition of individual growth cycles. See also Ritala, M., "Atomic Layer Deposition", p. 17-64, in Institute of Physics Series in Materials Science and Engineering "High-k Gate Dielectrics" edited by Michel Houssa, Institute of Physics Publishing, Bristol and Philadelphia 2003; Leskala, M., and Ritala, M., "ALD Precursor Chemistry: Evolution and Future Challenges," *J. Phys.* IV 9, p. 837-852, 1999.

Since a film deposited by ALD is grown in a layer-by-layer fashion and the total film thickness is given by the sum of the number of ALD cycles, it is possible to calculate the number of cycles necessary to reach a desired final film thickness. Conversely the thickness of a film can be set digitally by counting the number of reaction cycles. In general, ALD achieves deposition rates on the order of 0.1-1.0 Å per cycle, with cycle times ranging from one to ten seconds. Due to the self-limiting nature of the surface reactions, accidental overdosing with precursors does not result in increased film deposition. Thus, ALD is able to achieve very precise across-wafer film thickness uniformity, unmatched step coverage and exceptional conformality. Because of the nature of ALD, film thickness is immune to variations caused by non-uniform distribution of reactant vapor or temperature in the reaction chamber. See Niinisto, L., Paivasaari, J., Niinisto, J., Putkonen, M., and Mieminen, M., "Advance electronic and optoelectronic materials by Atomic Layer Deposition: An overview with special emphasis on recent progress in processing high-k dielectrics and other oxide materials", *Phys. Stat. Solid.* (a) 201, p. 1443-1452, (2004); Ritala, M., "Atomic layer deposition," Editors Michel Houssa, High-k Gate Dielectrics, p. 17-64, Publisher Institute of Physics Publishing, Bristol, UK, 2004; and; Liang, X., et al., "Synthesis of a Novel Porous Polymer/Ceramic Composite Material by Low-Temperature Atomic Layer Deposition," *Chem. Mater.* 19, P. 5388-5394, (2007).

A variety of chemical precursors may be used with ALD, depending upon the desired film. The general requirements and properties of useful chemical precursors are known. See Sneh, O., Clark-Phelps, R. B., Londergan, A. R., Winkler J., and Seidel, T., "Thin film atomic layer deposition equipment for semiconductor processing," *Thin Solid Films,* Vol. 402, Issues 1-2, p. 248-261, 2002 and Leskela, M., and Ritala, M., "Atomic Layer Deposition (ALD): from precursor to thin film structures,"*Thin Solid Films,* 409, p. 138-146, 2002.

The methods may include other steps. In some embodiments, the method further comprises coupling a light source to the first material. In other embodiments, the method further comprises coupling a programmable switching circuit to the light source. Any of the light sources, programmable switching circuits, and coupling techniques described above may be used.

Methods for Treating Wounds

Also disclosed are methods for treating a wound. The wound may be an open wound or a closed wound. By open wound it is meant a type of injury in which the skin of a subject is torn, cut, or punctured. By closed wound, it is meant a type of injury in which the skin of a subject may be damaged, but not necessarily broken. For example, blunt force trauma can result in a closed wound. The methods encompass treating one or more wounds of a variety of subjects. In some embodiments, the subject is a mammal. A variety of mammals may be treated including, but not limited to, humans.

In one embodiment, the method involves contacting any of the wound care systems disclosed above to a wound on a subject. In another embodiment, in which the wound care system comprises a light source coupled to the first material and a programmable switching circuit coupled to the light source, the method further comprises turning the light source on and off. The light source may be turned on whenever needed. For example, the light source may be turned on whenever bacteria growth increases or whenever the wound becomes more wet than desired. As described above, upon exposure to light, the bacterial growth will be inhibited and at least a portion of the liquid associated with the wound will be absorbed. In other embodiments, the light source may be turned on and off at predetermined intervals.

Additional Embodiments

As described above, the photocatalytic effect in $TiO_2$ is commonly activated by irradiation with ultraviolet light (UV light). For wound care applications it can be desirable to limit or eliminate the exposure of a patient's skin to potentially harmful UV rays when activating the bactericidal function of the ALD $TiO_2$ coated cotton fibers in wound care dressings or band aids. However, the use of $TiO_2$ as a photocatalyst can be somewhat limited by its bandgap and the rather quick recombination of excited electrons and holes.

$TiO_2$ only absorbs about 3% of the solar light and thus requires near-UV light to operate as an efficient photocatalyst. As described above, some wavelengths of light, for example UV light, can be dangerous to a patient's skin. Accordingly, it can be useful to extend the absorption range into the visible light region and to hinder electron-hole recombination. This can be achieved by doping with low-mass ions such as nitrogen and sulphur, or transition metal ions such as iron and cobalt. The visible light responsiveness and the active photocatalysis of $TiO_2$ under visible light rather than UV light can be significantly enhanced by doping the ALD $TiO_2$ thin films, for example, those ALD $TiO_2$ thin films described in embodiments herein, with a range of suitable dopants.

For activation, therefore, visible light electromagnetic radiation can be used which is detected by the human eye. The wavelengths can be, for example, about 390 nm to about 750 nm. Another embodiment for activation is longer wavelength radiation such as infrared (IR).

In some embodiments, nitrogen can be incorporated as a dopant into ALD $TiO_2$ thin films by adding nitrogen sources during the ALD growth process. In some embodiments, nitrogen can be incorporated by subsequent post-deposition nitridation annealing in a rapid annealing furnace under ammonia or nitrogen atmosphere, or multicharged ion deposition and implantation systems.

Generally, a large specific surface area is important to achieve high photocatalytic activities. For example, nanostructures such as, for example, nanotubes and nanofibrils have a particular advantage in the way they achieve high surface areas with three-dimensional mechanically coherent architectures that provide gas and radiation access.

In at least one of the embodiments, cotton fibers used in standard cotton wound dressing, or alternatively silk fibers or polymer fibers, or in the most general case any fibrous material, can be coated with doped $TiO_2$ ALD thin films thereby providing an enhanced, including greatly enhanced, surface area. This method can accomplish an ideal nanofibril surface morphology with greatly enhanced surface area.

Embodiments are not limited to those devices or methods described above. Additional embodiments include all applications where reduction or elimination of bacteria, for example, by minimizing bacteria growth rate, is preferred. Such embodiments may or may not require direct exposure of a wound or skin to light, for example, in the UV or visible light. Additional embodiments may incorporate the embodiments described above to be implemented for purposes of sterilizing laboratory equipment. For example, ALD $TiO_2$ may be coated onto cotton fabrics used in a medical setting that may require sterilization, for example, during surgery. Additional embodiments also include organic or inorganic fabrics, lab coats, paper, filters, porous glass filters, wound care dressings made from fibers other than cotton including polymer fibers, and equipment such as catheters and other surgical equipment that require sterilization after each use, each of which may be coated with ALD TiO2 thin films. Accordingly, other embodiments include sterilizing these ALD TiO2 thin film coated materials by using light, for example, UV light, to activate the photocatalytic effect.

In other embodiments, the materials described above may be coated with nitrogen doped ALD TiO2 thin films, thus allowing for activation of the photocatalytic effect with visible light instead of UV light. The materials comprising nitrogen doped ALD TiO2 thin film coatings can then be used directly on patient's skin, for example, as described in the various wound care applications of the embodiments disclosed herein. Thus, exposure of a patient's skin to potentially dangerous wavelengths of light may be avoided.

In other embodiments, the bactericidal effect of using $TiO_2$ for photocaltalytic oxidation of organic matter may be extended to the treatment of contaminated water. For example, filters such as water filters may be coated with ALD $TiO_2$ thin films (doped or undoped). In some embodiments, methods of sterilizing contaminated water are provided. These methods include the steps of flowing contaminated water through a filter comprising a coating of ALD TiO2 (doped or undoped) and simultaneously irradiating the water with UV light, visible light, or both as it passes through the filter.

Applications for embodiments described herein include, for example, water purification, air purification, self-cleaning coatings, sterilization, and disinfection.

All publications, patent applications, issued patents, and other documents referred to in this specification are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure. For the purposes of this disclosure and unless otherwise specified, "a" or "an" means "one or more."

What is claimed is:

1. An anti-bacterial article comprising:
a composite, the composite comprising
a first material,
wherein the first material comprises cotton, silk, a polymer, or a combination thereof
wherein the first material comprises a plurality of fibers;
wherein the first material has an absorbency for at least one fluid excreted from a wound;
a second material,
wherein the second material has a thickness ranging from about 5 nm to about 30 nm,
wherein the second material coats the fibers,
wherein the second material, upon exposure to light, inhibits the growth of bacteria on a surface of the composite,
wherein the second material, upon exposure to light, increases the absorbency of the first material;
a light source coupled to the composite; and
a programmable switching circuit coupled to the light source, wherein the programmable switch is programmed to turn the light source on and off at predetermined time intervals;

wherein the article is a wound care dressing.

2. The anti-bacterial article according to claim 1, wherein the second material comprises a metal oxide exhibiting a photocatalytic effect.

3. The anti-bacterial article according to claim 1, wherein the second material comprises $TiO_2$ or doped $TiO_2$.

4. The anti-bacterial article according to claim 1, wherein the second material comprises $TiO_2$ doped with an element selected from the group consisting of nitrogen, sulphur, a transition metal, and combinations thereof.

5. The anti-bacterial article according to claim 1, wherein the second material comprises $TiO_2$ doped with at least one transition metal selected from the group consisting of iron and cobalt.

6. The anti-bacterial article according to claim 1, wherein said light source produces visible light, UV light, or both.

7. The anti-bacterial article according to claim 6, wherein the light source is an artificial light source selected from the group consisting of fluorescent lamps, compact fluorescent lamps (CFLs), incandescent light bulbs, OLEDs, PLEDs, high pressure mercury lamps and halogen lamps.

8. A method of making the anti-bacterial article according to claim 1, comprising: coating the first material with the second material, wherein the second material, upon exposure to light, inhibits the growth of bacteria, increases the hydrophilicity of the first material, or both, and wherein the coating step comprises application of the second material comprising a technique selected from the group consisting of atomic layer deposition (ALD), vapor deposition methods, chemical vapor deposition, solution coating, and sol gel coating.

9. The method of making the anti-bacterial article according to claim 8, comprising, coating the first material with the second material using ALD.

10. The method of making the anti-bacterial article according to claim 9, wherein the second material comprises $TiO_2$ doped with an element selected from the group consisting of nitrogen, sulphur, a transition metal, and combinations thereof.

11. A method for sterilizing, comprising: providing an anti-bacterial article according to claim 1; and exposing the anti-bacterial article to light.

12. The method according to claim 11, further comprising:
applying said anti-bacterial article to a wound prior to the exposing step.

13. The method according to claim 12, wherein the second material comprises $TiO_2$ doped with an element selected from the group consisting of nitrogen, sulphur, a transition metal, and combinations thereof.

14. The method according to claim 13, wherein the second material, upon exposure to visible light, inhibits the growth of bacteria, increases the hydrophilicity of the first material, or both.

15. The method according to claim 14, wherein said exposing step comprises providing visible light from an artificial source selected from the group consisting of fluorescent lamps, compact fluorescent lamps (CFLs), incandescent light bulbs, OLEDs, PLEDs, high pressure mercury lamps and halogen lamps.

* * * * *